(12) United States Patent
Jaroch

(10) Patent No.: US 10,509,691 B2
(45) Date of Patent: Dec. 17, 2019

(54) TRACKING THE MENTAL ACUITY OF AN ELECTRONIC DEVICE USER

(71) Applicant: Colossio, Inc., Chicago, IL (US)

(72) Inventor: Joseph A. Jaroch, Chicago, IL (US)

(73) Assignee: Colossio, Inc., Chicago, IL (US)

( * ) Notice: Subject to any disclaimer, the term of this patent is extended or adjusted under 35 U.S.C. 154(b) by 86 days.

(21) Appl. No.: 15/794,660

(22) Filed: Oct. 26, 2017

(65) Prior Publication Data
US 2019/0129766 A1     May 2, 2019

(51) Int. Cl.
*G06F 9/54*     (2006.01)
*G06N 20/00*     (2019.01)
*G06F 16/951*     (2019.01)

(52) U.S. Cl.
CPC ............ *G06F 9/542* (2013.01); *G06F 16/951* (2019.01); *G06N 20/00* (2019.01)

(58) Field of Classification Search
CPC .................................................... G06F 9/542
USPC ......................................................... 719/318
See application file for complete search history.

(56) References Cited

U.S. PATENT DOCUMENTS

| | | | |
|---|---|---|---|
| 2005/0183143 A1* | 8/2005 | Anderholm | G06F 11/32 726/22 |
| 2006/0184410 A1* | 8/2006 | Ramamurthy | G06Q 10/10 706/8 |
| 2017/0116552 A1* | 4/2017 | Deodhar | G06Q 10/06316 |
| 2018/0011978 A1* | 1/2018 | Reeckmann | G06N 5/04 |

* cited by examiner

*Primary Examiner* — Andy Ho
(74) *Attorney, Agent, or Firm* — Barnes & Thornburg LLP

(57) ABSTRACT

A method including retrieving, from an operating system of a client device, a timestamp associated with a physical action on an input device coupled with the client device, is provided. The method includes tagging the timestamp with an action metadata of an application running in the client device, the physical action being associated with the application, and forming an aggregated dataset comprising the timestamp and the action metadata. The method also includes associating an acuity value to the timestamp based on the aggregated dataset, and modifying a display of an application output to indicate the acuity value within the application. A system and a non-transitory, computer readable medium storing instructions to perform the method are also provided.

20 Claims, 9 Drawing Sheets

TRACKING THE MENTAL ACUITY OF AN ELECTRONIC DEVICE USER

BACKGROUND

Field

The present disclosure generally relates to tracking the mental acuity of an electronic device user. More specifically, the present disclosure relates to tracking the mental acuity of a user accessing one or more applications in a computer.

Description of the Related Art

Today, there exist multiple tests for evaluating and assessing the mental acuity of a person. Many degrees of automation may be found in current techniques. However, a common shortcoming of currently existing techniques is the lack of spontaneity for the person being evaluated (e.g., test "anxiety"), the invasiveness of the procedure, and the lack of a continuous flow of accurate data over an extended period of time. Currently, there exists no method to passively track mental acuity without inconveniencing the user or producing test anxiety.

SUMMARY

In one embodiment of the present disclosure, a computer-implemented method is described. The computer-implemented method includes retrieving, from an operating system of a client device, a timestamp associated with a physical action on an input device coupled with the client device, tagging the timestamp with an action metadata of an application running in the client device, the physical action being associated with the application, and forming an aggregated dataset comprising the timestamp and the action metadata. The computer-implemented method also includes associating an acuity value to the timestamp based on the aggregated dataset, and modifying a display of an application output to indicate the acuity value within the application.

According to one embodiment, a system is described that includes one or more processors and a memory coupled to the one or more processors, the memory including instructions that, when executed by the one or more processors, cause the one or more processors to retrieve, from an operating system of a client device, a timestamp associated with a physical action on an input device coupled with the client device, to tag the timestamp with an action metadata of an application running in the client device, the physical action being associated with the application. The one or more processors also execute instructions to form an aggregated dataset comprising the timestamp and the action metadata, to associate an acuity value to the timestamp based on the aggregated dataset, and to modify a display of an application output to indicate the acuity value within the application.

According to one embodiment, a non-transitory, machine readable medium is described that includes instructions, which when executed by one or more processors, cause a computer to perform a method. The method includes retrieving, from an operating system of a client device, a timestamp associated with a physical action on an input device coupled with the client device, tagging the timestamp with an action metadata of an application running in the client device, the physical action being associated with the application, and forming an aggregated dataset comprising the timestamp and the action metadata. The method also includes associating an acuity value to the timestamp based on the aggregated dataset, and modifying a display of an application output to indicate the acuity value within the application.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and, together with the description, serve to explain the principles of the disclosed embodiments. In the drawings.

In the figures, elements and steps denoted by the same or similar reference numerals are associated with the same or similar elements and steps, unless indicated otherwise.

DETAILED DESCRIPTION

Figure 1:
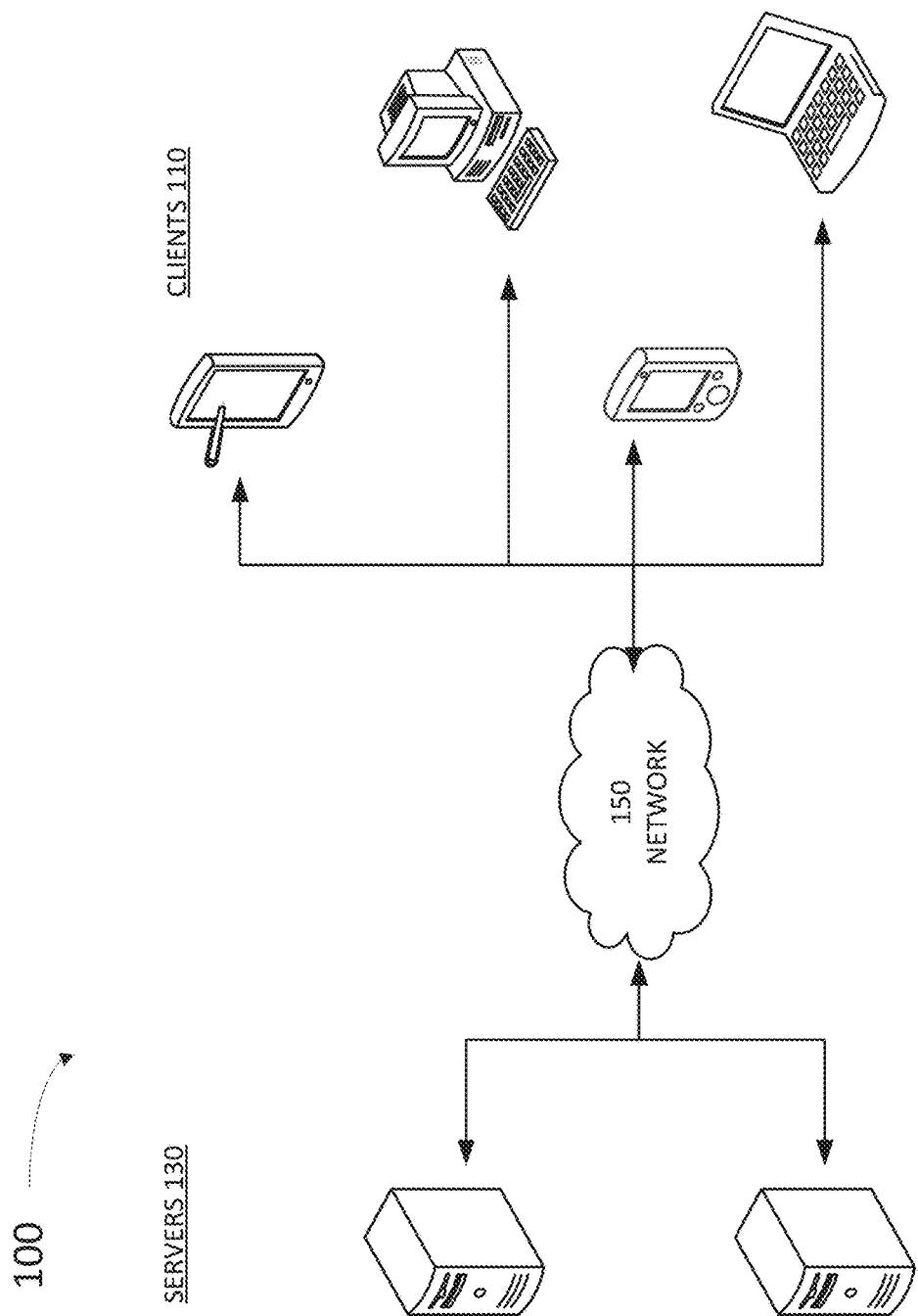
FIG. 1 illustrates an example architecture suitable for tracking a mental acuity of a user, according to some embodiments.

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

General Overview

Embodiments as disclosed herein enable the measurement of a user acuity while using an electronic device in a seamless, spontaneous and non-invasive manner, over extended periods of time. By passively assessing acuity, a more reliable profile of the user of an electronic device or appliance can be established, ensuring that degradations in acuity are identified early.

Attributed to natural aging or underlying conditions, mental acuity can vastly change over a person's lifetime. Modern medicine has recognized that early identification of mental degradation results in an elongation of positive mental performance. However, current standard annual screening processes leave room for error and often miss subtle changes which can quickly become exacerbated into a broader decline in performance. On a smaller scale, mental acuity varies throughout the day, whether due to drifting thoughts, insufficient sleep, or a variety of other causes which can dramatically impact job performance. As a person becomes tired, work product quality tends to suffer. As an example, in the software field, more mistakes may be introduced into a codebase when attentiveness wanes.

Evaluation of the mental acuity of an electronic device user is of interest for industries that rely heavily on work product that is derived from the electronic devices. For example, software development companies whose employees create thousands or millions of lines of code every week, are heavily invested in the reduction of errors produced by inattentiveness, because these errors typically translate into long, inefficient debugging sessions. Another area where real-time, accurate evaluation and assessment of mental acuity is the care for elderly or mentally ill people, e.g., in nursing homes, psychiatric wards, hospitals and the like. Companies that rely on employees constantly supervising a stream of data and taking critical actions based on the observed data trends may use embodiments consistent with the present disclosure, e.g., stock trading firms, airport control towers, 911 responders, and other law enforcement or private security personnel in charge of surveillance devices.

The disclosed system addresses the problem of lack of spontaneity, invasiveness, and the lack of continuity over extended periods of time for acuity evaluation of people, which is a problem specifically arising in the realm of computer technology, by providing a solution also rooted in computer technology, namely, by identifying metadata from the interaction of a user with a computer and tagging a timestamp for each of the actions in the interaction between the user and the computer.

The proposed solution further provides improvements to the functioning of the computer itself because it saves computer usage and computational time (e.g., substantially reducing debugging time for software developers and the like).

Although many examples provided herein describe a user's search inputs being identifiable, or user to electronic device interaction history, each user may grant explicit permission for such user information to be shared or stored. The explicit permission may be granted using privacy controls integrated into the disclosed system. Each user may be provided notice that such user information will be shared with explicit consent, and each user may at any time end having the information shared, and may delete any stored user information. The stored user information may be encrypted to protect user security.

Example System Architecture

FIG. 1 illustrates an example architecture 100 for tracking a mental acuity of a user, according to some embodiments. Architecture 100 includes servers 130 and clients 110 connected over a network 150. One of the many servers 130 is configured to host a memory including instructions which, when executed by a processor, cause the server 130 to perform at least some of the steps in methods as disclosed herein. In some embodiments, the processor is configured to tag selected activity in client device 110 and retrieve a timestamp from it. Accordingly server 130 may evaluate the tagged activity and determine a level of acuity of the user of client device 110. For purposes of load balancing, multiple servers 130 can host memories including instructions to one or more processors and multiple servers 130 can host the collection of images.

Servers 130 may include any device having an appropriate processor, memory, and communications capability for hosting an acuity engine that may collect acuity data from a user and perform a statistical analysis on the acuity data. Server 130 may then store the statistical analysis in a database within the server or accessible to server 130 through network 150. In some embodiments, server 130 uses information from the database to perform the statistical analysis and other processing of the acuity data (e.g., user interaction history from the instant user, or from multiple users). The acuity engine is accessible by various clients 110 over the network 150. Clients 110 can be, for example, desktop computers, mobile computers, tablet computers (e.g., including e-book readers), mobile devices (e.g., a smartphone or PDA), or any other devices having appropriate processor, memory, and communications capabilities for accessing the acuity engine on one of servers 130. Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like.

Example System

Figure 2:
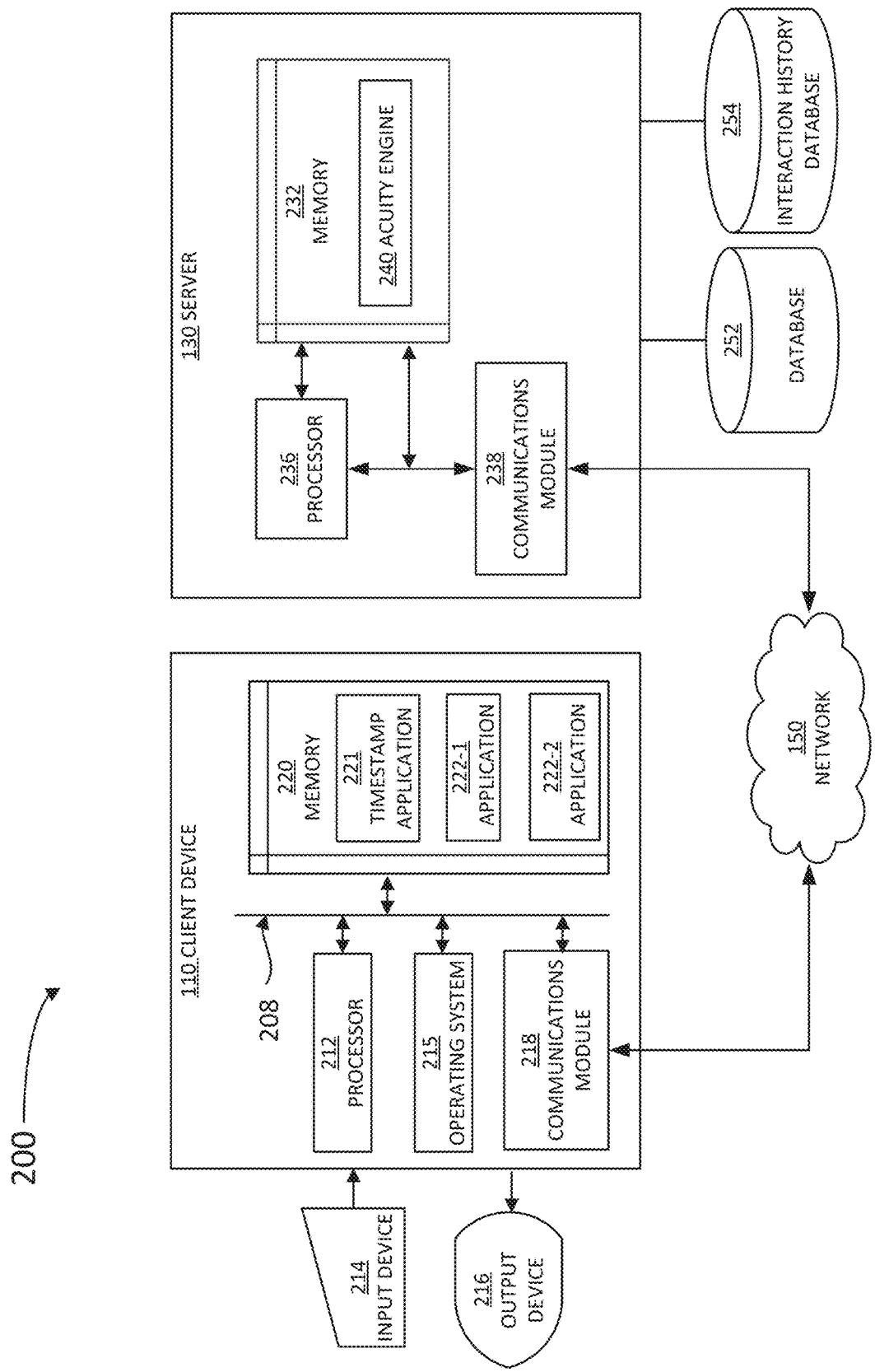
FIG. 2 is a block diagram illustrating an example server and a client device from the architecture of FIG. 1, according to certain aspects of the disclosure.

FIG. 2 is a block diagram 200 illustrating an example server 130 and client 110 in the architecture 100 of FIG. 1, according to certain aspects of the disclosure. Client 110 and server 130 are communicatively coupled over network 150 via respective communications modules 218 and 238. Communications modules 218 and 238 are configured to interface with network 150 to send and receive information, such as data, requests, responses, and commands to other devices on the network. Communications modules 218 and 238 can be, for example, modems or Ethernet cards.

Client device 110 includes a processor 212, an operating system (OS) 215, a communications module 218, and a memory 220, all communicatively coupled with each other through a bus line 208. Memory 220 may include several application, installed in client device 110, such as a timestamp application 221 and other functional applications 222-1 and 222-2 (hereinafter, collectively referred to as "functional applications 222"). Client device 110 may also include or be communicatively coupled with an input device 214 and an output device 216. Input device 214 may include a keyboard or a touchscreen (in which case input device 214 and output device 216 may be part of the same device), a mouse, a pointer, and the like. Embodiments as disclosed herein include determining a change in mental acuity of a user accessing client device 110 through input device 214, based on the speed between strokes on a keyboard, taps on a touch screen, movements of a mouse, and other input actions that are timestamped and recorded by timestamp application 221.

Server 130 includes a memory 232, a processor 236, and a communications module 238. Server 130 also includes an acuity engine 240. Processor 236 is configured to interact with, and execute instructions from, acuity engine 240. Acuity engine 240 may execute commands stored in memory 232, and retrieve/store data from and to memory 232. Server 130 also includes, or may be coupled with, a database 252, and an interaction history recipient 254. In one or more implementations, database 252 represents a database that contains data units and associated information regarding the data units, such as statistical analysis and location information for the data unit within a document.

In some embodiments, database 252 and interaction history recipient 254 may be external to server 130, for example, they can be hosted in a memory of a different server but accessible by server 130. For example, in some embodiments, database 252 and interaction history recipient 254 may be remotely accessible to server 130 through network 150. In some embodiments, database 252 and interaction history recipient 254 may be internal to server 130. Database 252 may include any one of a structured query language (SQL) database, a not-only-SQL (NoSQL) database, a MySQL database, and the like. Interaction history recipient 254 may include prior parsing results that acuity engine 240 may use for further applications to shorten the processing. For example, when acuity engine 240 is used for parsing text rich documents, access to results obtained from prior documents may be relevant for acuity engine 240 to determine a frequency score for certain words in a sentence (e.g., in an English document). In some embodiments, when acuity engine 240 is used to parse a genome to determine certain disease patterns and the like, acuity engine 240 may use prior genomes stored in interaction history recipient 254 so as to strengthen the scoring capability for the frequency of newly introduced genomes. Server 130 may access time stamp application 221 in client device 110 through acuity engine 240, or through a web browser installed in client device 110.

Figure 3:
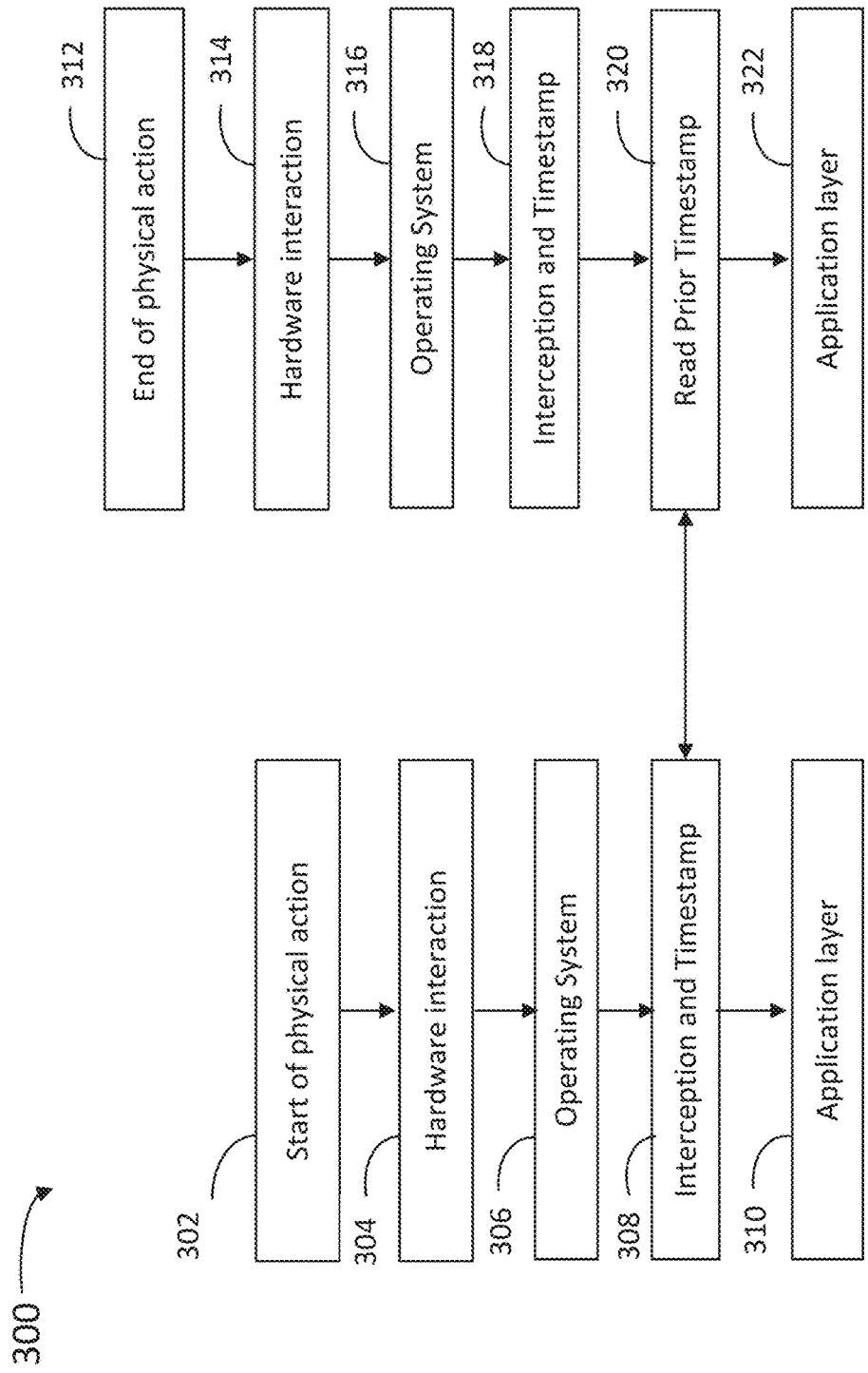
FIG. 3 is a block diagram illustrating steps and hardware in a computer-user interaction tagged with start and end timestamps, according to some embodiments.

Processor 212 in client device 110 executes instructions stored in timestamp application 221 to perform a majority of control and timestamp routines consistent with methods disclosed herein. Client device 110 may include low-level system instrumentation such as device drivers (e.g., for a keyboard, a mouse, a touchscreen display, and the like), coupling to, or performing other interception strategies to monitor user actions in client device 110. This allows for accurate timestamp calculation between events. Further, in some embodiments, data aggregation and posterior analysis from the finely granular data collected by client device 110 may be performed by processor 236 executing instructions from acuity engine 240, in server 130. User input events (e.g., "user activity") are packaged together and sent from client device 110 to server 130 for processing, display, and storage, using communications modules 218 and 238, via network 150. Server 130 receives the data via a POST request and stores it in database 252. In some embodiments, data pertaining to each user is stored separately to allow for individualized reports to be produced FIG. 3 is a block diagram 300 illustrating steps and hardware in a computer-user interaction tagged with start and end timestamps, according to some embodiments. Timestamps are calculated and persisted at the start and end of a physical action, wherein the physical action is associated with an input user activity, e.g., a key stroke, a mouse motion, a mouse click, or a finger swipe on a touchscreen display. In block 302 a physical action is started (e.g., a user presses a key on a keyboard). In block 304, a hardware component included in, or associated with, client device 110 (e.g., the keyboard, input device 214) detects the physical action, and transmits a detection signal to OS 215 in block 306.

OS 215 intercepts the detection signal from the hardware in block 308 and issues a timestamp. In some embodiments, in block 308 the system identifies a context for the physical action as actions are occurring to determine whether the user is switching between windows (e.g., between different functional applications 222) or when they have stopped/started a particular gesture. Further, block 308 may include timestamps associated with varying types of physical actions (switching from keyboard to mouse, or drawing vs tapping)

A similar sequence of events is registered in blocks 312, 314, 316 and 318 for ending the physical action (e.g., removing the finger from the pressed keystroke position to release the key). The duration of events or physical actions is identified by determining the difference between timestamps from block 308 and from block 318, in block 320. This gives a tangible data point to identify the lingering time on each keystroke or mouse click for a given user of client device 110. Active processes are found using functions from OS 215 that enumerate active windows/applications to identify what the user is actively working on when input time samples are gathered, in application layer blocks 310 and 322 (e.g., the user is typing text on the keyboard for a Word® application, a C++ compiler, an e-mail application, and the like).

Figure 4:
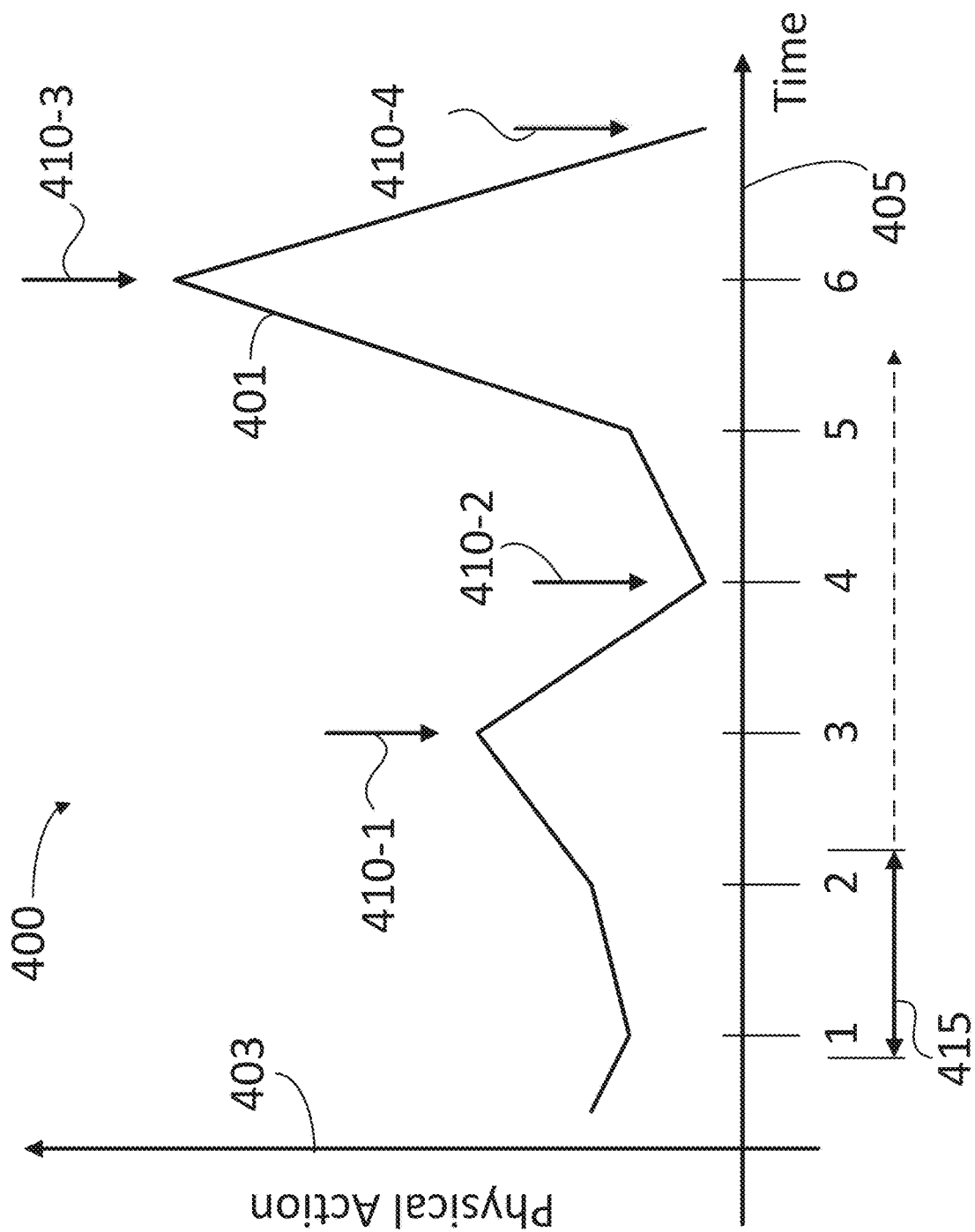
FIG. 4 is a chart illustrating tagged user actions as a function of time to determine a mental acuity, according to some embodiments

FIG. 4 is a chart 400 illustrating tagged user actions 403 as a function of time 405 to determine a mental acuity, according to some embodiments. In some embodiments, a curve 401 may be obtained by aggregating the tagged activities of the user as reported by the operating system over a time period indicated by a time stamp. In some embodiments, it is desirable that the resolution of the timestamps be less than 1 millisecond (1 ms=$10^{-3}$ secs.), such as 100 nanoseconds (1 ns=$10^{-9}$ secs.), or less.

Curve 401 may be provided by acuity engine 240 in server 130, or may be provided to acuity engine 240 by timestamp application 221 in client device 110. Accordingly, in some embodiments acuity engine 240 performs a multilinear regression, a principal component analysis, a nonlinear, neural network, or a deep learning neural network to determine an acuity level based on the number of activities in curve 401. In some embodiments, acuity engine 240 may also use a rate of activity level (e.g., time derivative of curve 401) as a factor to determine the acuity level. Curve 401 may be associated to a specific functional application 222 that the user of client device 110 has accessed. For example, certain functional applications 222 may involve a heavier physical activity, e.g., a graphic editing engine may require precise and well-timed clicks, and other mouse gestures such as: click-hold, click-release. In some embodiments, acuity engine 240 may store into database 252 multiple curves 401, each associated with a user of a client device 110. Accordingly, a curve 401 may include data for a user accessing client device 100 to run one or more functional applications 222.

Further, in some embodiments, multiple curves 401 for a given user may be stored as historical data in interaction history database 254. In that regard, acuity engine 240 may store data "localized" over shorter periods of time in database 252. In some embodiments, acuity engine 240 may store "globalized" data associated with a user over months or years. Accordingly, acuity engine 240 may evaluate impact of certain quotidian events (e.g., sleeping habits, eating habits, and the like) for the user, or other, longer-term events (e.g., ageing, disease, and the like).

Curve 401 illustrates a series of clearly identifiable events 410-1, 410-2, 410-3, and 410-4 (hereinafter, collectively referred to as "events 410") where the activity level increases or decreases substantively. For example, events 410-1 and 410-3 may be associated with increased acuity of the user, while events 410-2 and 410-4 may be associated with a decrease in acuity. Accordingly, in some embodiments chart 400 may be useful to determine the type and pattern of events associated with increased acuity (e.g., desirable in some applications), such as time of the week, correlation seasonal data, and the like. Thus, a company or institution may derive strategies to improve and maximize the quality of work output by employees based on conclusions derived from curve 401 in chart 400.

For example, in some embodiments curve 401 may indicate a significant dropout event 410-4 occurring, e.g., every Friday, in a software development company. The managers may decide then to implement more strict quality performance tests to be provided on Fridays, or on Mondays, to ensure a reduced number of returned products.

In some embodiments, curve 401 may include one or more reference frames (e.g., time windows). Tracking mental acuity over a plurality of reference frames is implemented by storing and analyzing the timestamps associated with a moving window of activity 415. Accordingly, time stamp application 221 or acuity engine 240 may be configured to identify idle periods with zero, or very low physical action and remove these periods from curve 401. In some embodiments, curve 401 is locally stored in memory 220, at least temporarily. Further, in some embodiments, memory 220 is periodically synchronized (e.g., in real, or semi-real time) with database 252 in server 130. In some embodiments, curve 401 may be written to local memory 220 for temporary buffering when connectivity to network 150 is unavailable. Eventually, curve 401 is uploaded to server 130 with an identifier associated with client device 110. Accordingly, server 130 is able to track activity across a plurality of client devices 110 belonging to a particular user, or multiple users.

In some embodiments, a relative level of mental acuity may be associated with the active task being performed (e.g., the ordinate in FIG. 4) by spawning an asynchronous thread upon each interaction with the device which receives information about the active process, task, or window (e.g., the one or more functional applications 222). Accordingly, in some embodiments multiple curves 401 may be generated and stored, each curve corresponding to a different functional application 222 accessed by the user of client device 110. The multiple curves 401 may be interleaved in time, e.g., when a user continually shifts from one functional application 222 to another, during a certain time window 415. Such may be the case, for example, when a user is typing an extensive Word document, or C++ code, and interrupting the work with occasional web browsing activity.

In some embodiments, acuity engine 240 and/or timestamp application 221 may also keep track of context for each of these actions. As users of client device 110 go about their daily duties, acuity engine 240 and/or timestamp application 221 identifies for which functional applications 222 the user types more slowly, how the user typing speed changes throughout the course of the day, and how their reaction time varies based on the content of the work.

Further, in some embodiments acuity engine 240 and/or timestamp application 221 may be configured to identify idle time, switching time between keyboard/mouse, or a duration it takes to physically transition to different points on screen (starting to move the mouse, aiming toward the destination, and ultimately stopping at the appropriate point). Over the course of the day, observed values will vary depending on alertness, caffeine consumption, and type of work. When code is checked in, aggregate results may be stored, allowing a manager or code reviewer to look at the produced visualizations (e.g., curve 401) and correlate them with what code was being worked on throughout the day.

Figure 5:
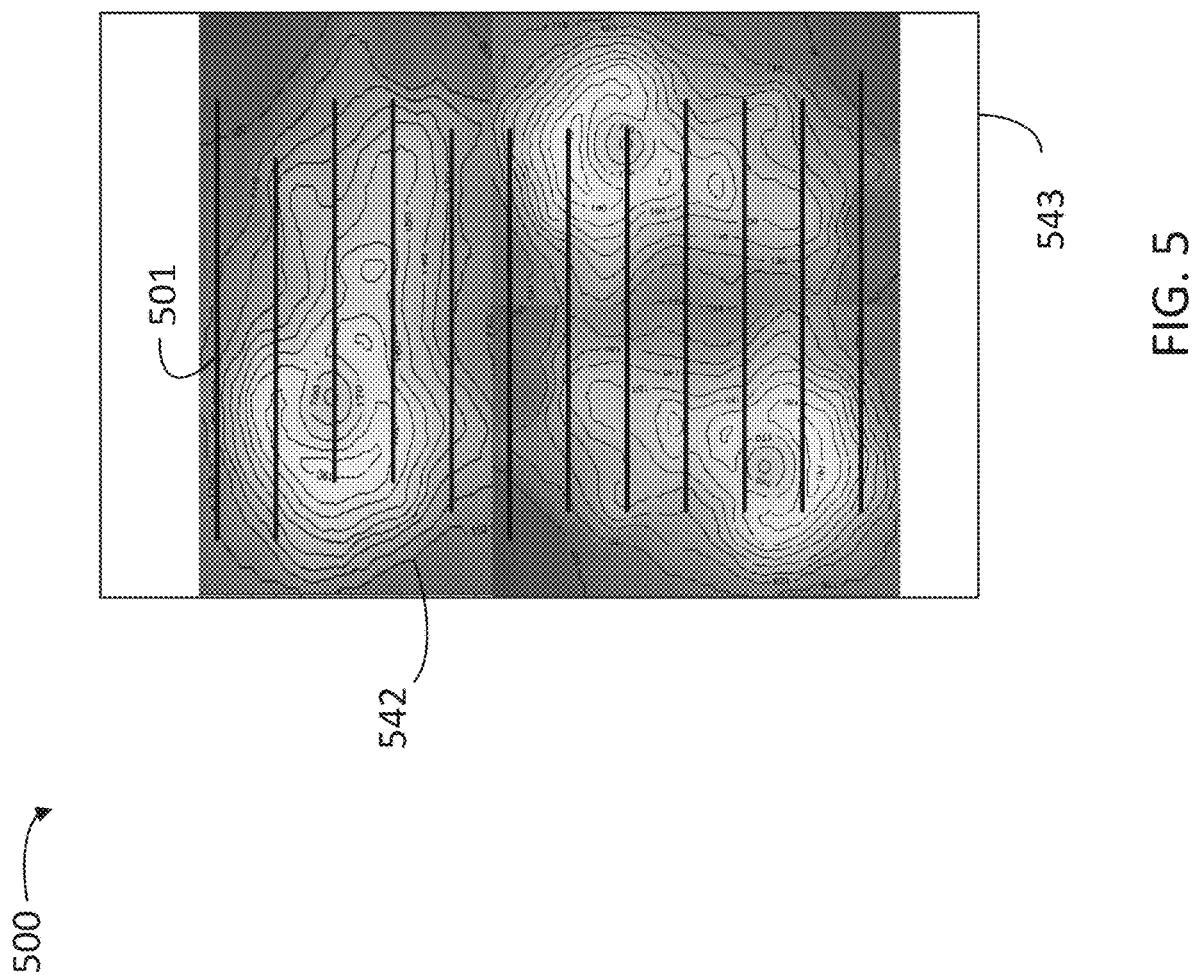
FIG. 5 is an example of a heat map overlay indicating a mental acuity while a user interacts with a document, according to some embodiments.

FIG. 5 is an example of a heat map overlay 500 indicating a mental acuity while a user interacts with a document 543, according to some embodiments. In some embodiments, document 543 may be a computer code including command lines 501, or a text in a rich-text editor. Accordingly, as the user types in each of the lines 501 in document 543, timestamp application 221 and acuity engine 240 may determine an acuity level of the user in real-time, or quasi real-time. Thus, processor 212 or 236 may evaluate contour lines 542, indicating points within document 543 wherein the measured user acuity level is the same. The heat map includes multiple loops formed by multiple contour lines 542. In some embodiments, a lighter color in heat map overlay 500 indicates a higher acuity level, and a darker color indicates a lower acuity level.

Document 543 may be computer code produced by a software engineering firm that has encountered lapses in quality and are looking to mitigate this problem. The software engineering firm may have a large staff and the quality drop may not be clearly attributable to any individual software developer. Accordingly, the software engineering firm may install acuity engine 240 in a central server 130, and a timestamp application 221 in each of the individual workstations for the engineers. Accordingly, and consistent with embodiments disclosed herein, acuity engine 240 passively monitors one or more of the employees in the firm. The monitoring may include taking two snapshots on each hardware action: identifying when a key is pressed down and when it is released, and identifying when a mouse is clicked down and released (cf. FIG. 3). A curve with physical activity over time (e.g., curve 401) may be created, stored, and transmitted to server 130.

Heat map overlay 500 indicates where (and when) key travel speed decreased (not necessarily overall typing speed, but the time it takes to release the finger from a button) and where (and when) alertness was reduced which indicates areas that could be more susceptible to errors and may call for additional consideration.

Figure 6:
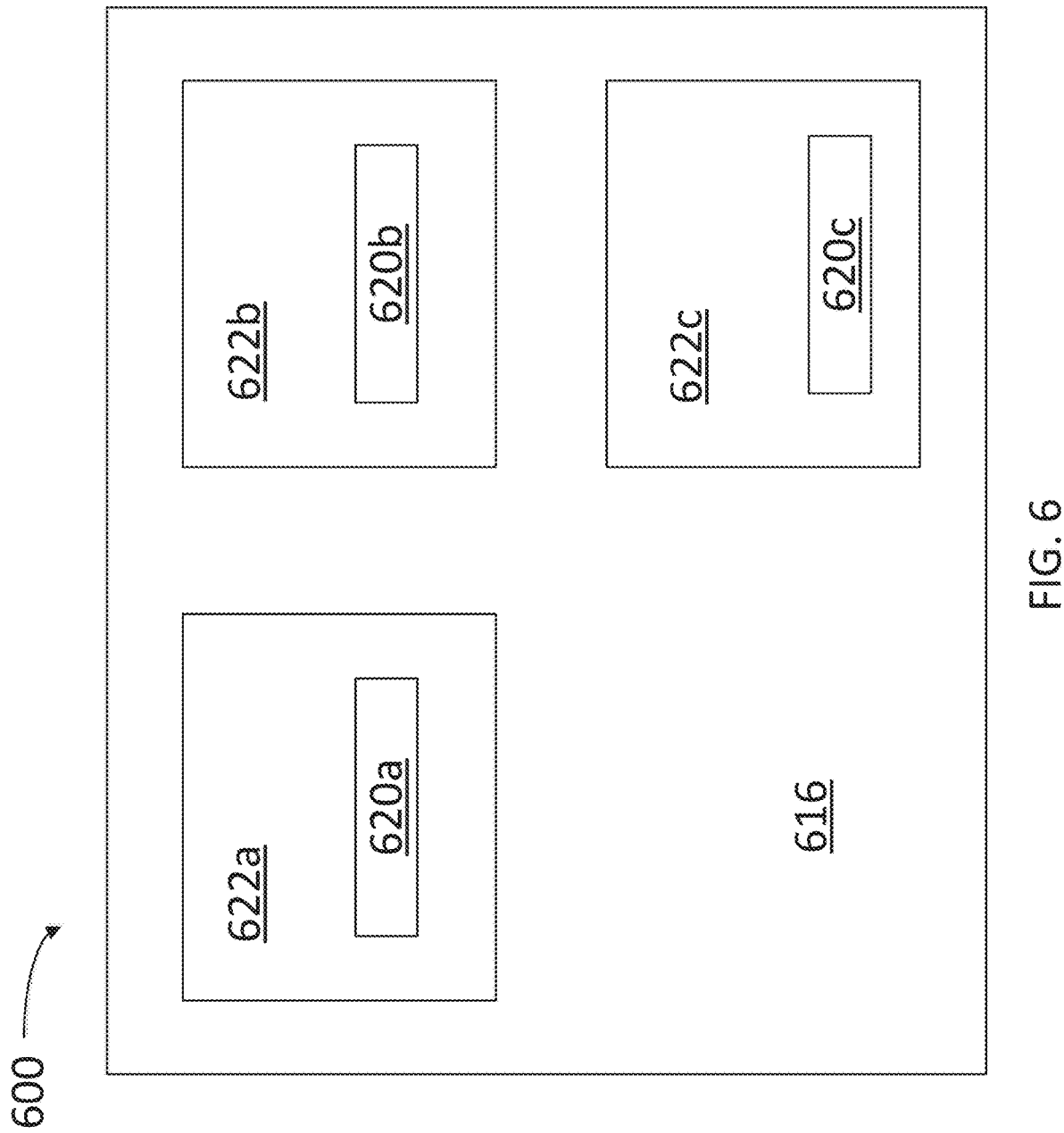
FIG. 6 illustrates a display including multiple windows running different applications for a user in an electronic device, according to some embodiments.

FIG. 6 illustrates a display 600 in an output device 616 including multiple windows 622a, 622b, and 622c (hereinafter, collectively referred to as "windows 622") running different applications (e.g., functional applications 222) in a system for tracking mental acuity of a user interacting with a client device (e.g., client device 110), according to some embodiments. Output device 616 may be integrated into, or externally coupled with a client device as disclosed herein (e.g., output device 216 and client device 110). Each of applications 622 may include a child component 620a, 620b, and 620c (hereinafter, collectively referred to as "child components 620"), respectively. Further, applications 622 may be different webpages from an internet browsing application, and child components 620 may include a search tab on each of the different web pages.

In a configuration as illustrated in display 600, an acuity engine as disclosed herein may track independently the user interaction with each of applications 622, and identify, for each interaction, the child component 620 accessed by the user. Further, in some embodiments the acuity engine may combine the user interaction with all of applications 622 and provide an aggregated analysis for the user acuity. In some embodiments, the acuity engine may collect data associated with the shifting of the user from one application (e.g., application 622a) to another application (622b, or 622c). Accordingly, in some embodiments a multilinear regression algorithm, a principal components algorithm, or a neural network algorithm may recognize and weigh more heavily or less heavily application shifting events to evaluate an acuity score for the user.

Figure 7:
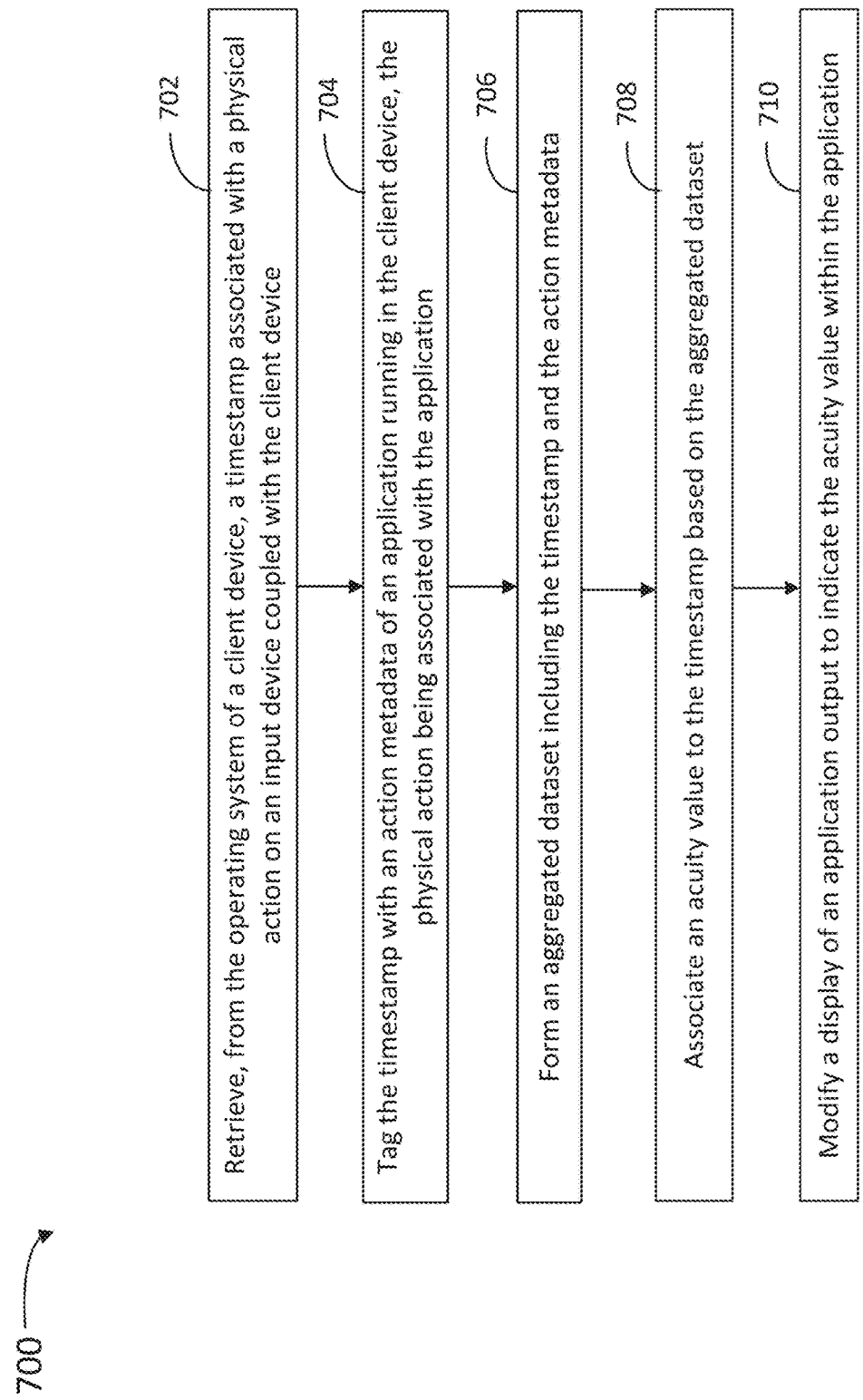
FIG. 7 is a flow chart illustrating steps in a method for intercepting and tagging a user activity, according to some embodiments.

FIG. 7 is a flow chart illustrating steps in a method 700 for intercepting and tagging a user activity, according to some embodiments. Method 700 may be performed at least partially by any one of client devices (e.g., any one of servers 130 and any one of clients 110) communicating with any one of network servers. The client devices may be handled by a user, wherein the user may be registered to a private account with the server, or may be a visitor to the server website or logged in a server application installed in the client device. The user may interact with the client device via an input device that may be integrated to the client device, or communicatively coupled with it (e.g., input device 214). At least some of the steps in method 700 may be performed by a computer having a processor executing commands stored in a memory of the computer (e.g., processors 212 and 236, memories 220 and 232). Further, steps as disclosed in method 700 may include retrieving, editing, and/or storing files in a database that is part of, or is communicably coupled to, the computer, using, inter-alia, an acuity engine, or a timestamp application (e.g., database 252, interaction history database 254, acuity engine 240 and timestamp application 221). Moreover, steps in methods consistent with method 700 may include the timestamp application communicating with an operative system in the client device to retrieve a timestamp and other metadata associated with one or more functional applications run by the user in the client device (e.g., operating system 215 and functional applications 222). Methods consistent with the present disclosure may include at least some, but not all, of the steps illustrated in method 700, performed in a different sequence. Furthermore, methods consistent with the present disclosure may include at least two or more steps as in method 700 performed overlapping in time, or almost simultaneously.

Step 702 includes retrieving, from the operating system of a client device, a timestamp associated with a physical action on an input device coupled with the client device. In some embodiments, step 702 includes determining a time lapse between a first timestamp for a start of the physical action and a second timestamp for an end of the physical action. In some embodiments, the physical action on an input device may include keystrokes pressed on a keyboard, taps on a touch screen, movements of a mouse, or other input actions using a device driver or system level filter.

Step 704 includes tagging a timestamp with action metadata of an application running in the client device, the physical action being associated with the application. The action metadata may include the specific application accessed by the user of the client device, the version (e.g., "Word 2.0," "Adobe Acrobat 6.0," and the like), and other related metadata. In some embodiments, step 704 includes transmitting the timestamp to the server, the timestamp including a user identification for the user of the client device.

Step 706 includes forming an aggregated dataset including the timestamp and the action metadata. In some embodiments, step 706 includes sending the timestamp to an active processor. In some embodiments, step 706 includes sending the timestamp to the processor in the client device. In some embodiments, step 706 includes sending the timestamp to the processor in the server. In some embodiments, step 706 includes collecting multiple timestamps from multiple applications installed in the client device. In some embodiments, step 706 includes incorporating the physical action to a histogram of activity with a time partition comprising a bin size greater than a timestamp resolution of the operating system.

Step 708 includes associating an acuity value to the timestamp based on the aggregated dataset. In some embodiments, step 708 includes determining a rate of the physical action from the aggregated dataset. In some embodiments, step 708 includes identifying a change in mental acuity of a user. Accordingly, step 708 may include identifying the speed and acceleration between physical input actions. Further, in some embodiments step 708 may include applying a frequency analysis to the aggregated data. For example, in some embodiments step 708 may include applying a Fourier transform to the aggregated data to find one or more frequency components in the aggregated data, indicative of the acuity value. In some embodiments, step 708 includes applying at least one of a multi-linear regression, a principal components analysis, and a nonlinear machine learning algorithm to the aggregated dataset to determine the acuity value. In some embodiments, step 708 includes tracking the mental acuity across a plurality of reference frames or time windows, to identify variation within a single day as well as variation across many weeks. In some embodiments, step 708 includes transmitting the timestamp and a user identification of the client device to a remote server, the remote server configured to collect multiple aggregated datasets from multiple users associated with multiple client devices, and to determine the acuity value based on the multiple aggregated datasets; and receiving the acuity value from the remote server.

In some embodiments, step 708 includes generating a cryptographic hash of mental acuity data and storing the cryptographic hash alongside each timestamp entry in the database. The cryptographic hash may be associated to a user ID from client device 110 for privacy purposes. In some embodiments, step 708 may include storing collected data in multiple levels to allow for specificity of analysis. Accordingly, step 708 may include associating the acuity data with the specific current page or document, at one level. At a second level, step 708 may include associating the acuity data with the functional application or window used by the user of the client device at the time the physical activity data was collected. At yet another level, step 708 may include associating the acuity data to a specific time frame or window, regardless of the functional application running at the time when the acuity data was collected.

Step 710 includes modifying a display of an application output to indicate the acuity value within the application. In some embodiments, step 710 includes collecting multiple timestamps and tags to form an aggregated dataset. In some embodiments, step 710 includes collecting multiple acuity values and identifying an event strongly correlated with a high acuity value. In some embodiments, step 710 includes associating the relative level of mental acuity with the active task being performed by the user to later pinpoint areas more likely to contain faults due to a lessened mental state during the task. In some embodiments, step 710 includes inducing an occurrence of an event that is strongly correlated with a high acuity value. In some embodiments, step 710 includes regularly passively assessing user acuity.

Figure 8:
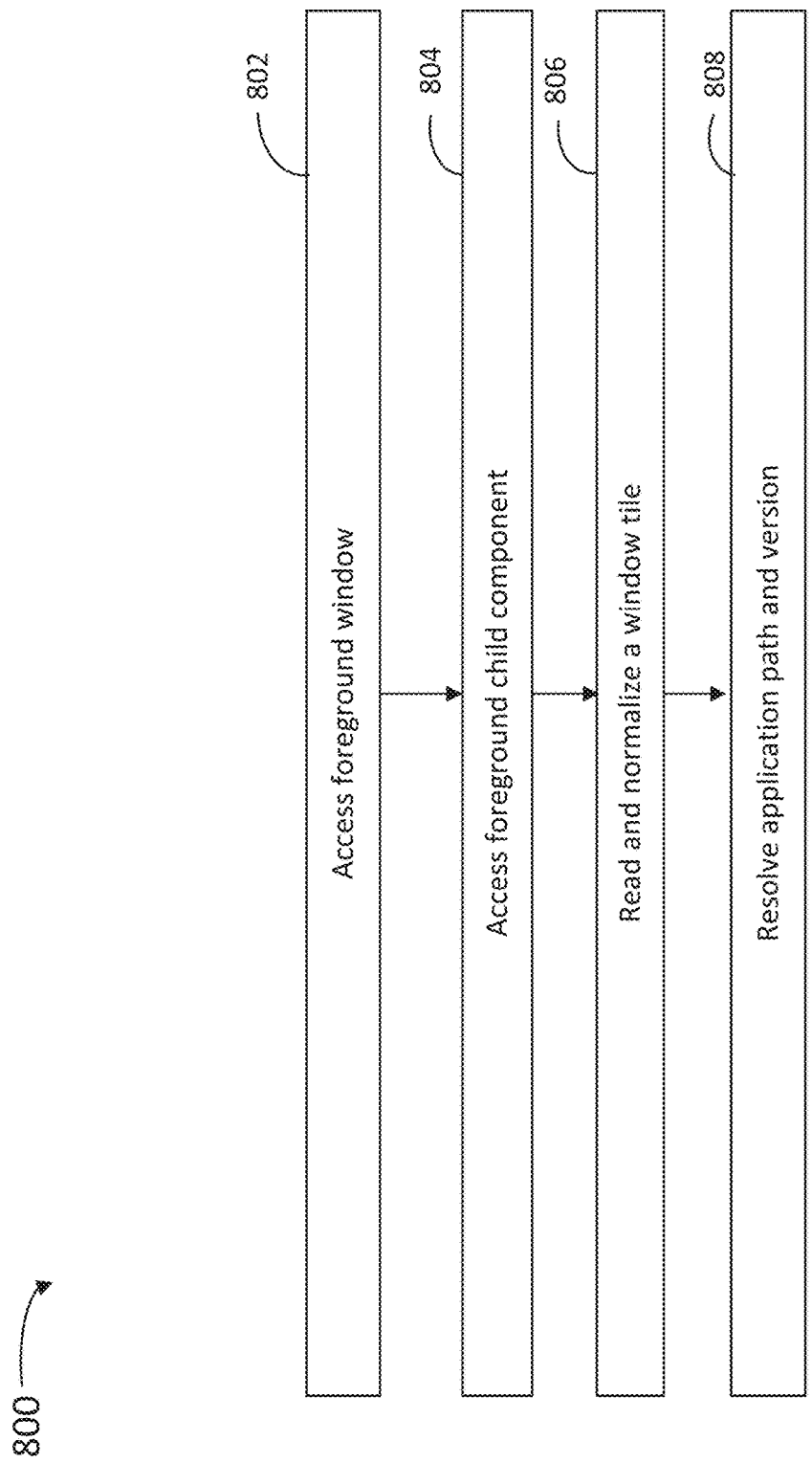
FIG. 8 is a flow chart illustrating an asynchronous thread to determine a mental acuity, according to some embodiments.

FIG. 8 is a flow chart illustrating a method 800 including an asynchronous thread to determine a mental acuity, according to some embodiments. Method 800 may be performed at least partially by any one of client devices (e.g., any one of servers 130 and any one of clients 110) communicating with any one of network servers hosting a timestamp application and a plurality of functional applications in the client device (e.g., timestamp application 221 and functional applications 222). The client devices may be handled by a user, wherein the user may be registered to a private account with the server, or may be a visitor to the server website or logged in the timestamp application or the functional application installed in the client device. At least some of the steps in method 800 may be performed by a computer having a processor executing commands stored in a memory of the computer (e.g., processors 212 and 236, memories 220 and 232). Further, steps as disclosed in method 800 may include retrieving, editing, and/or storing files in a database that is part of, or is communicably coupled to, the computer, using, inter-alia, an acuity engine, or a timestamp application (e.g., database 252, interaction history database 254, acuity engine 240 and timestamp application 221). Moreover, steps in methods consistent with method 800 may include the timestamp application communicating with an operative system in the client device to retrieve a timestamp and other metadata associated with one or more functional applications run by the user in the client device (e.g., operating system 215 and functional applications 222). Methods consistent with the present disclosure may include at least some, but not all, of the steps illustrated in method 800, performed in a different sequence. Furthermore, methods consistent with the present disclosure may include at least two or more steps as in method 800 performed overlapping in time, or almost simultaneously.

Step 802 includes accessing a foreground window.

Step 804 includes accessing a foreground child component in the window.

Step 806 includes reading and normalizing a window tile.

Step 808 includes resolving an application path and version.

Hardware Overview

Figure 9:
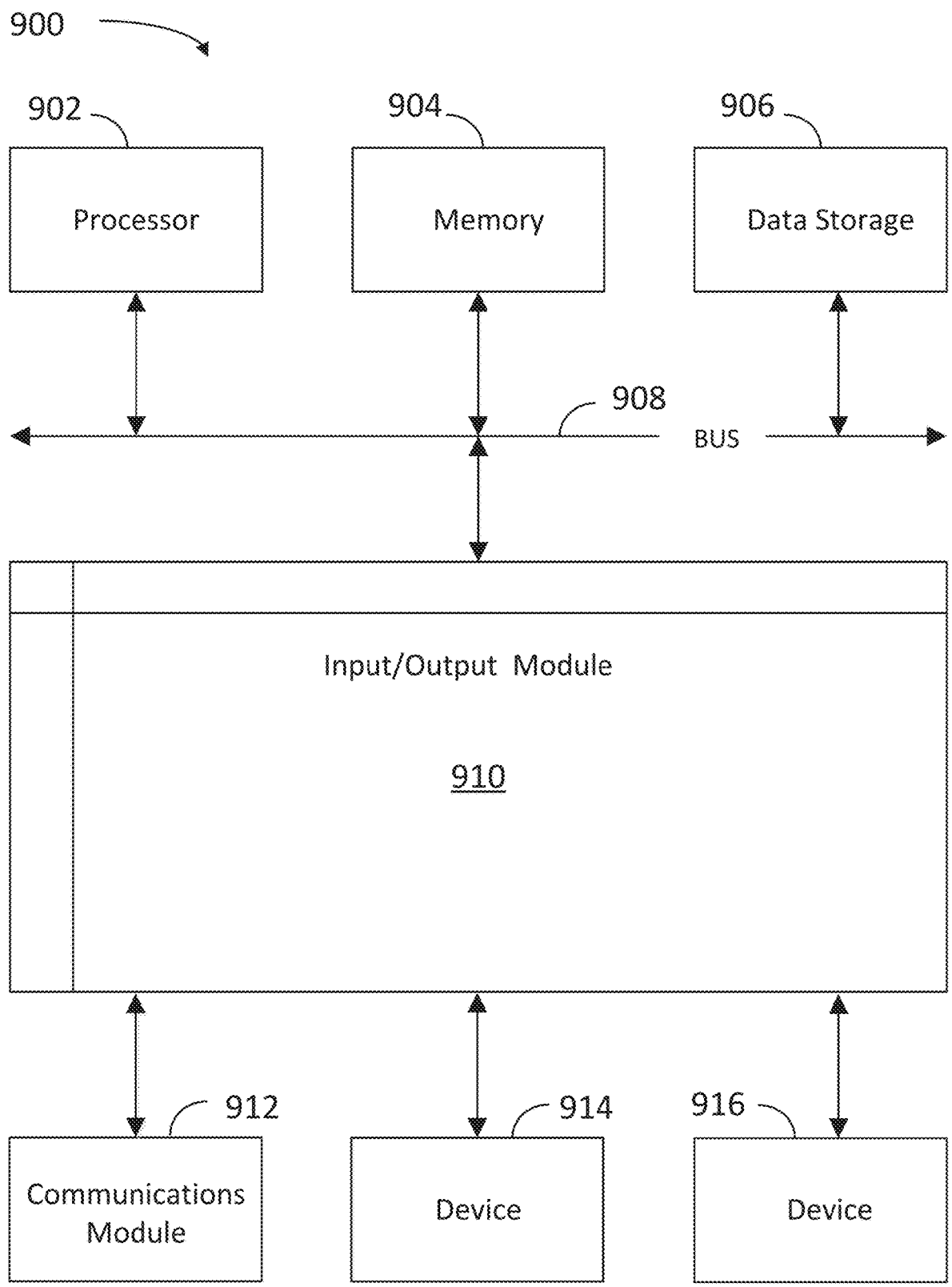
FIG. 9 is a block diagram illustrating an example computer system with which the client and server of FIGS. 1 and 2, and the methods of FIGS. 5 and 6 can be implemented, according to some embodiments.

FIG. 9 is a block diagram illustrating an exemplary computer system 900 with which the client 110 and server 130 of FIGS. 1 and 2, and the methods of FIGS. 7 and 8, can be implemented. In certain aspects, the computer system 900 may be implemented using hardware or a combination of software and hardware, either in a dedicated server, or integrated into another entity, or distributed across multiple entities.

Computer system 900 (e.g., client 110 and server 130) includes a bus 908 or other communication mechanism for communicating information, and a processor 902 (e.g., processors 212 and 236) coupled with bus 908 for processing information. By way of example, the computer system 900 may be implemented with one or more processors 902. Processor 902 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 900 can include, in addition to hardware, a code that creates an execution environment for the computer program in question, e.g., code that constitutes processor firmware, a protocol stack, a database management system, an operating system, or a combination of one or more of them stored in an included memory 904 (e.g., memories 220 and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 908 for storing information and instructions to be executed by processor 902. The processor 902 and the memory 904 can be supplemented by, or incorporated in, a special purpose logic circuitry.

The instructions may be stored in the memory 904 and implemented in one or more computer program products, i.e., one or more modules of computer program instructions encoded on a computer readable medium for execution by, or to control the operation of, the computer system 900, and according to any method well known to those skilled in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 904 may also be used for storing temporary variable or other intermediate information during execution of instructions to be executed by processor 902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 900 further includes a data storage device 906, such as a magnetic disk or optical disk, coupled to bus 908 for storing information and instructions. Computer system 900 may be coupled via input/output module 910 to various devices. Input/output module 910 can be any input/output module. Exemplary input/output modules 910 include data ports, such as USB ports. The input/output module 910 is configured to connect to a communications module 912. Exemplary communications modules 912 (e.g., communications modules 218 and 238) include networking interface cards, such as Ethernet cards and modems. In certain aspects, input/output module 910 is configured to connect to a plurality of devices, such as an input device 914

(e.g., input device 214) and/or an output device 916 (e.g., output device 216). Exemplary input devices 914 include a keyboard and a pointing device, e.g., a mouse or a trackball, by which a user can provide input to the computer system 900. Other kinds of input devices 914 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 716 include display devices, such as an LCD (liquid crystal display) monitor, for displaying information to the user.

According to one aspect of the present disclosure, the client 110 and server 130 can be implemented using a computer system 900 in response to processor 902 executing one or more sequences of one or more instructions contained in memory 904. Such instructions may be read into memory 904 from another machine-readable medium, such as data storage device 706. Execution of the sequences of instructions contained in main memory 904 causes processor 702 to perform the process steps described herein. One or more processors in a multi-processing arrangement may also be employed to execute the sequences of instructions contained in memory 904. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. The communication network (e.g., network 150) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 900 can include clients and servers. A client and server are generally remote from each other and typically interact through a communication network. The relationship of client and server arises by virtue of computer programs running on the respective computers and having a client-server relationship with each other. Computer system 900 can be, for example, and without limitation, a desktop computer, laptop computer, or tablet computer. Computer system 900 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer readable medium" as used herein refers to any medium or media that participates in providing instructions to processor 902 for execution. Such a medium may take many forms, including, but not limited to, non-volatile media, volatile media, and transmission media. Non-volatile media include, for example, optical or magnetic disks, such as data storage device 906. Volatile media include dynamic memory, such as memory 904. Transmission media include coaxial cables, copper wire, and fiber optics, including the wires that comprise bus 908. Common forms of machine-readable media include, for example, floppy disk, flexible disk, hard disk, magnetic tape, any other magnetic medium, CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of X, Y, and Z" or "at least one of X, Y, or Z" each refer to only X, only Y, or only Z; any combination of X, Y, and Z; and/or at least one of each of X, Y, and Z.

To the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products. Other variations are within the scope of the following claims.

What is claimed is:

1. A computer-implemented method, comprising:
    retrieving, from an operating system of a client device, a timestamp associated with a physical action on an input device coupled with the client device;
    tagging the timestamp with an action metadata of an application running in the client device, the physical action being associated with the application;
    forming an aggregated dataset comprising the timestamp and the action metadata;
    generating an acuity value based on the aggregated dataset;
    associating the acuity value to the timestamp; and
    generating an application output of the application that indicates the acuity value associated with one or more portions of the application output.

2. The computer-implemented method of claim 1, wherein retrieving a timestamp associated with a physical action on an input device coupled with the client device comprises determining a time lapse between a first timestamp for a start of the physical action and a second timestamp for an end of the physical action.

3. The computer-implemented method of claim 1, wherein the retrieving, from the operating system of the client device, the timestamp associated with a physical action on an input device comprises sending the timestamp to a processor that is executing the application running in the client device.

4. The computer-implemented method of claim 1, wherein forming the aggregated dataset comprises collecting multiple timestamps from multiple applications installed in the client device.

5. The computer-implemented method of claim 1, wherein associating an acuity value to the timestamp based on the action metadata and the aggregated dataset comprises determining a rate of the physical action from the aggregated dataset.

6. The computer-implemented method of claim 1, wherein associating an acuity value to the timestamp based on the action metadata and the aggregated dataset comprises applying at least one of a multi-linear regression, a principal components analysis, and a nonlinear machine learning algorithm to the aggregated dataset to determine the acuity value.

7. The computer-implemented method of claim 1, wherein associating an acuity value to the timestamp based on the action metadata and the aggregated dataset comprises:
    transmitting the timestamp and a user identification of the client device to a remote server, the remote server configured to collect multiple aggregated datasets from multiple users associated with multiple client devices, and to determine the acuity value based on the multiple aggregated datasets; and
    receiving the acuity value from the remote server.

8. The computer-implemented method of claim 1, wherein forming an aggregated dataset comprises including the physical action in a histogram of activity with a time partition comprising a bin size greater than a timestamp resolution of the operating system.

9. The computer-implemented method of claim 1, further comprising collecting multiple acuity values and identifying an event strongly correlated with a high acuity value.

10. The computer-implemented method of claim 1, further comprising inducing an occurrence of an event that is strongly correlated with a high acuity value.

11. A system comprising:
    one or more processors; and
    a memory coupled to the one or more processors, the memory including instructions that, when executed by the one or more processors, cause the one or more processors to:
        retrieve, from an operating system of a client device, one or more timestamps associated with one or more physical actions on an input device coupled with the client device;
        tag the timestamp with an action metadata of an application running in the client device, the one or more physical actions being associated with the application;
        form an aggregated dataset comprising the timestamp and the action metadata;
        generate a mental acuity value associated with each of the one or more timestamps and based on the aggregated dataset wherein the mental acuity value indicates a mental acuity of a user operating the input device; and
        modify a display of an application output to indicate the mental acuity value for each of the timestamps within the application.

12. The system of claim 11, wherein to retrieve a timestamp associated with a physical action on an input device coupled with the client device, the one or more processors execute instructions to determine a time lapse between a first timestamp for a start of the physical action and a second timestamp for an end of the physical action.

13. The system of claim 11, wherein to associate an acuity value to the timestamp based on the action metadata and the aggregated dataset, the one or more processors execute instructions to determine a rate of the physical action from the aggregated dataset.

14. The system of claim 11, wherein to associate an acuity value to the timestamp based on the action metadata and the aggregated dataset the one or more processors execute instructions to apply at least one of a multi-linear regression, a principal components analysis, and a nonlinear machine learning algorithm to the aggregated dataset to determine the acuity value.

15. The system of claim 11, wherein to form the aggregated dataset the one or more processors execute instructions to collect multiple timestamps from multiple applications installed in the client device.

16. The system of claim 11, wherein to associate an acuity value to the timestamp based on the action metadata and the aggregated dataset the one or more processors execute instructions to:
  transmit the timestamp and a user identification of the client device to a remote server, the remote server configured to collect multiple aggregated datasets from multiple users associated with multiple client devices, and to determine the acuity value based on the multiple aggregated datasets; and
  receive the acuity value from the remote server.

17. The system of claim 11, wherein to retrieve, from the operating system of the client device, the timestamp associated with a physical action on an input device the one or more processors execute instructions to send the timestamp to a processor that is executing the application running in the client device.

18. The system of claim 11, wherein to form an aggregated dataset the one or more processors execute instructions to include the physical action in a histogram of activity with a time partition comprising a bin size greater than a timestamp resolution of the operating system.

19. A non-transitory, computer readable medium comprising instructions which, when executed by a processor in a computer, cause the computer to execute a method, the method comprising:
  retrieving continuously, from an operating system of a client device, a timestamp associated with a physical action on an input device coupled with the client device;
  tagging the timestamp with an action metadata of an application running in the client device, the physical action being associated with the application;
  forming an aggregated dataset with the timestamp and the action metadata;
  associating, in real-time, an acuity value to the timestamp based on the aggregated dataset; and
  modifying a display of an application output to indicate the acuity value within the application.

20. The non-transitory, computer-readable medium of claim 19, wherein the method comprises retrieving a timestamp associated with a physical action on an input device coupled with the client device comprises determining a time lapse between a first timestamp for a start of the physical action and a second timestamp for an end of the physical action.

* * * * *